US009604066B2

(12) United States Patent
Carbunaru et al.

(10) Patent No.: US 9,604,066 B2
(45) Date of Patent: Mar. 28, 2017

(54) SYSTEMS AND METHODS FOR IMPROVING RF COMPATIBILITY OF ELECTRICAL STIMULATION LEADS

(71) Applicant: BOSTON SCIENTIFIC NEUROMODULATION CORPORATION, Valencia, CA (US)

(72) Inventors: Rafael Carbunaru, Valley Village, CA (US); Matthew Lee McDonald, Pasadena, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 868 days.

(21) Appl. No.: 13/896,109

(22) Filed: May 16, 2013

(65) Prior Publication Data
US 2013/0310900 A1  Nov. 21, 2013

Related U.S. Application Data

(60) Provisional application No. 61/649,090, filed on May 18, 2012.

(51) Int. Cl.
| A61N 1/372 | (2006.01) |
| A61N 1/05 | (2006.01) |
| A61N 1/375 | (2006.01) |
| A61N 1/08 | (2006.01) |

(52) U.S. Cl.
CPC .......... *A61N 1/372* (2013.01); *A61N 1/0551* (2013.01); *A61N 1/375* (2013.01); *A61N 2001/086* (2013.01)

(58) Field of Classification Search
CPC .................. A61N 2001/086; A61N 1/3752
See application file for complete search history.

(56) References Cited

U.S. PATENT DOCUMENTS

| 6,181,969 B1 | 1/2001 | Gord |
| 6,516,227 B1 | 2/2003 | Meadows et al. |
| 6,609,029 B1 | 8/2003 | Mann et al. |
| 6,609,032 B1 | 8/2003 | Woods et al. |
| 6,741,892 B1 | 5/2004 | Meadows et al. |
| 7,244,150 B1 | 7/2007 | Brase et al. |
| 7,437,193 B2 | 10/2008 | Parramon et al. |
| 7,672,734 B2 | 3/2010 | Anderson et al. |

(Continued)

*Primary Examiner* — Michael Kahelin
(74) *Attorney, Agent, or Firm* — Lowe Graham Jones PLLC; Bruce E. Black

(57) ABSTRACT

An implantable lead assembly for an electrical stimulation system includes a first lead configured for insertion into a patient. A current-limiting arrangement is coupleable with the first lead. The current-limiting arrangement is configured for limiting the amount of RF-induced current propagating along a body of the first lead during an MRI procedure. The current-liming arrangement includes a safety device configured to couple to the lead body when the lead body is implanted in the patient. The safety device defines a first port extending along a length of the safety device. The first port is configured for receiving a proximal end portion of the lead body and covering each of multiple terminals disposed along the lead body to prevent the terminals from contacting patient tissue. The safety device provides an impedance of at least 50 ohms at one or more MRI RF frequencies.

20 Claims, 10 Drawing Sheets

(56) References Cited

U.S. PATENT DOCUMENTS

| | | |
|---|---|---|
| 7,761,165 B1 | 7/2010 | He et al. |
| 7,949,395 B2 | 5/2011 | Kuzma |
| 7,974,706 B2 | 7/2011 | Moffitt et al. |
| 8,000,801 B2 † | 8/2011 | Stevenson |
| 8,175,710 B2 | 5/2012 | He |
| 8,224,450 B2 | 7/2012 | Brase |
| 8,364,278 B2 | 1/2013 | Pianca et al. |
| 2007/0150036 A1 | 6/2007 | Anderson |
| 2010/0174349 A1* | 7/2010 | Stevenson ............ G01R 33/285 607/116 |
| 2013/0116765 A1* | 5/2013 | Osypka ................ A61N 1/3752 607/119 |

\* cited by examiner
† cited by third party

SYSTEMS AND METHODS FOR IMPROVING RF COMPATIBILITY OF ELECTRICAL STIMULATION LEADS

CROSS-REFERENCE TO RELATED APPLICATIONS

This application claims the benefit under 35 U.S.C. §119 (e) of U.S. Provisional Patent Application Ser. No. 61/649,090 filed on May 18, 2012, which is incorporated herein by reference.

FIELD

The present invention is directed to the area of implantable electrical stimulation systems and methods of making and using the systems. The present invention is also directed to safety devices coupleable to implanted electrical stimulation leads that reduce at least one potentially unsafe condition occurring during exposure of a patient to applied electromagnetic fields, as well as methods of making and using the safety devices, leads, and electrical stimulation systems.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

Conventional implanted electrical stimulation systems are often incompatible with magnetic resonance imaging ("MRI") due to the large radio frequency ("RF") pulses used during MRI. The RF pulses can generate transient signals in the conductors and electrodes of an implanted lead. These signals can have deleterious effects including, for example, unwanted heating of the tissue causing tissue damage, induced currents in the lead, or premature failure of electronic components.

BRIEF SUMMARY

In one embodiment, an implantable lead assembly for an electrical stimulation system includes a first lead configured and arranged for insertion into a patient. The first lead includes a lead body having a distal end portion, a proximal end portion, and a longitudinal length; a plurality of electrodes disposed along the distal end portion of the lead body; a plurality of terminals disposed along the proximal end portion of the lead body; and a plurality of conductors electrically coupling the plurality of electrodes to the plurality of terminals. A current-limiting arrangement is coupleable with the first lead. The current-limiting arrangement is configured and arranged for limiting the amount of RF-induced current propagating along the lead body during an MRI procedure. The current-liming arrangement includes a safety device configured and arranged to couple to the lead body when the lead body is implanted in the patient. The safety device has a length and an outer surface. The safety device defines a first port extending along the length of the safety device. The first port is configured and arranged for receiving the proximal end portion of the lead body and for covering each of the plurality of terminals to prevent the plurality of terminals from contacting patient tissue. The safety device provides an impedance of at least 50 ohms at one or more MRI RF frequencies.

In another embodiment, a method for protecting a patient with an implanted medical device from current propagation along the medical device during exposure to applied electromagnetic fields during an MRI procedure includes inserting a lead into a patient. The lead includes a lead body having a distal end portion, a proximal end portion, and a longitudinal length; a plurality of electrodes disposed along the distal end portion of the lead body; a plurality of terminals disposed along the proximal end portion of the lead body; and a plurality of conductors electrically coupling the plurality of electrodes to the plurality of terminals. A safety device of a current-limiting arrangement is coupled to the lead body. The current-limiting arrangement is configured and arranged for limiting the amount of RF-induced current propagating along the lead body during an MRI procedure. The safety device has a length and an outer surface. The safety device defines a first port extending along the length of the safety device. The first port is configured and arranged for receiving the proximal end portion of the lead body and for covering each of the plurality of terminals to prevent the plurality of terminals from contacting patient tissue. The safety device provides an impedance of at least 50 ohms at one or more MRI RF frequencies. An MRI procedure is performed on the patient while the safety device is coupled to the lead body. The safety device is removed from the lead body within three months of coupling the safety device to the lead body.

In yet another embodiment, an implantable lead assembly for an electrical stimulation system includes a first lead configured and arranged for insertion into a patient. The first lead includes a lead body having a distal end, a proximal end, and a longitudinal length; a plurality of electrodes disposed on the distal end of the lead body; a plurality of terminals disposed on the proximal end of the lead body; and a plurality of conductors electrically coupling the plurality of electrodes to at least one of the terminals. A current-limiting arrangement is coupleable with the first lead. The current-limiting arrangement is configured and arranged for limiting the amount of RF-induced current propagating along the lead body during an MRI procedure. The current-liming arrangement includes a safety device configured and arranged to couple to the lead body when the lead body is implanted in the patient. The safety device has a length and an outer surface. The safety device defines a first port extending along the length of the safety device. The first port is configured and arranged for receiving the proximal end of the lead body and for covering each of the plurality of terminals to prevent the plurality of terminals from contacting patient tissue. The safety device provides an impedance of at least 50 ohms at one or more MRI RF frequencies. The safety device is configured and arranged to at least partially extend externally from the patient when the safety device is coupled to the lead body.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to safety devices coupleable to implanted electrical stimulation leads that reduce at least one potentially unsafe condition occurring during exposure of a patient to applied electromagnetic fields, as well as methods of making and using the safety devices, leads, and electrical stimulation systems.

Suitable implantable electrical stimulation systems include, but are not limited to, an electrode lead ("lead") with one or more electrodes disposed on a distal end of the lead and one or more terminals disposed on one or more proximal ends of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,244,150; 7,672,734; 7,761,165; 7,949,395; 7,974,706; 8,175,710; and 8,364,278; and U.S. Patent Application Publication No. 2007/0150036, all of which are incorporated by reference.

Figure 1:
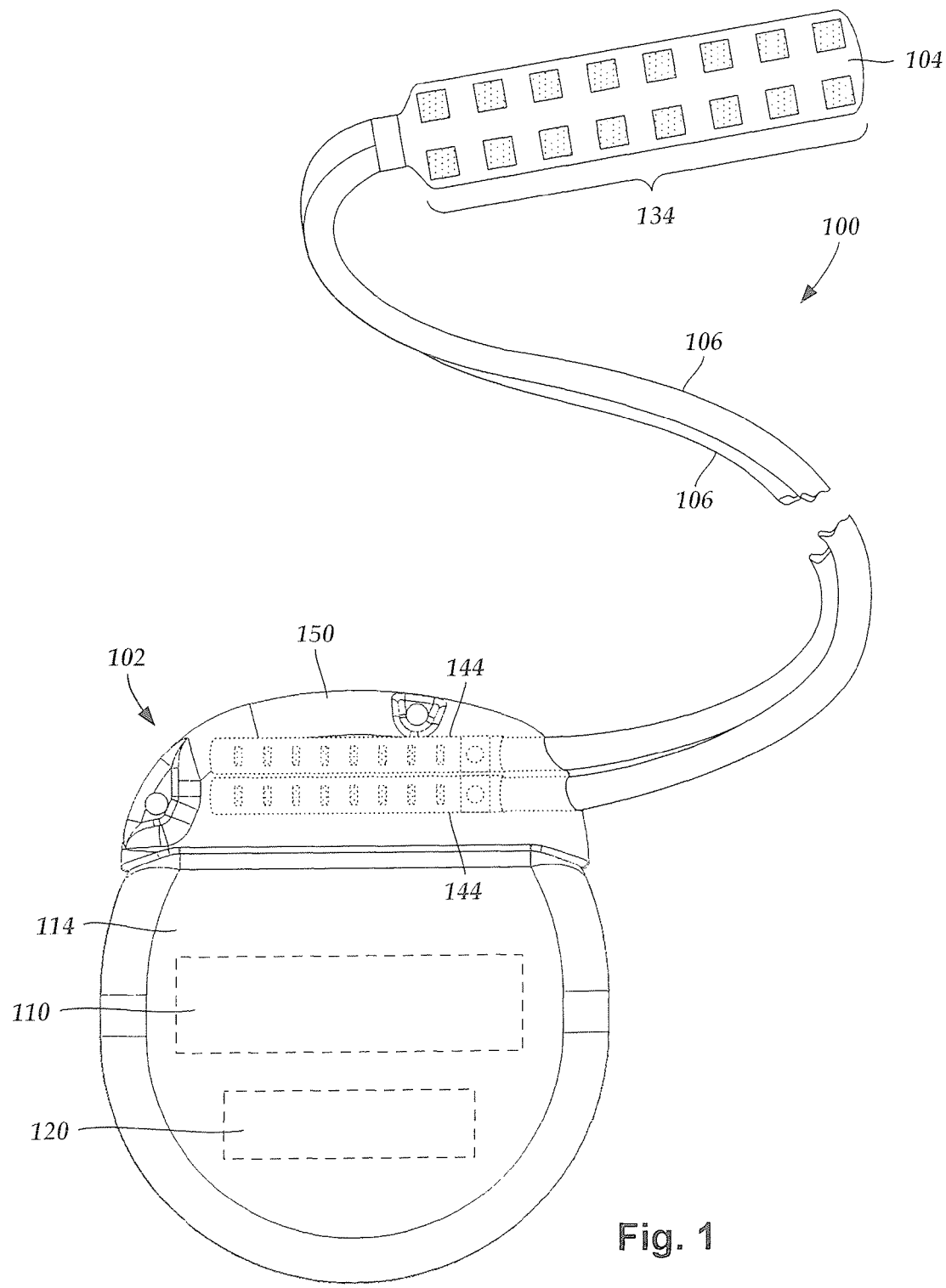
FIG. 1 is a schematic view of one embodiment of an electrical stimulation system that includes a paddle lead with a paddle body coupled to a control module via lead bodies, according to the invention.

FIG. 1 illustrates schematically one embodiment of an electrical stimulation system 100. The electrical stimulation system includes a control module (e.g., a stimulator or pulse generator) 102, a paddle body 104, and one or more lead bodies 106 coupling the control module 102 to the paddle body 104. The paddle body 104 and the one or more lead bodies 106 form a lead. The paddle body 104 typically includes an array of electrodes 134. The control module 102 typically includes an electronic subassembly 110 and an optional power source 120 disposed in a sealed housing 114. In FIG. 1, two lead bodies 106 are shown coupled to the control module 102.

The control module 102 typically includes one or more connector assemblies 144 into which the proximal end of the one or more lead bodies 106 can be plugged to make an electrical connection via connector contacts (e.g., 316 in FIGS. 3A-3B; and 340 of FIG. 3C) disposed in the connector assembly 144 and terminals (e.g., 310 in FIGS. 3A-3C) on each of the one or more lead bodies 106. The connector contacts are coupled to the electronic subassembly 110 and the terminals are coupled to the electrodes 134. In FIG. 1, two connector assemblies 144 are shown.

The one or more connector assemblies 144 may be disposed in a header 150. The header 150 provides a protective covering over the one or more connector assemblies 144. The header 150 may be formed using any suitable process including, for example, casting, molding (including injection molding), and the like. In addition, one or more lead extensions 324 (see FIG. 3C) can be disposed between the one or more lead bodies 106 and the control module 102 to extend the distance between the one or more lead bodies 106 and the control module 102.

Figure 2:
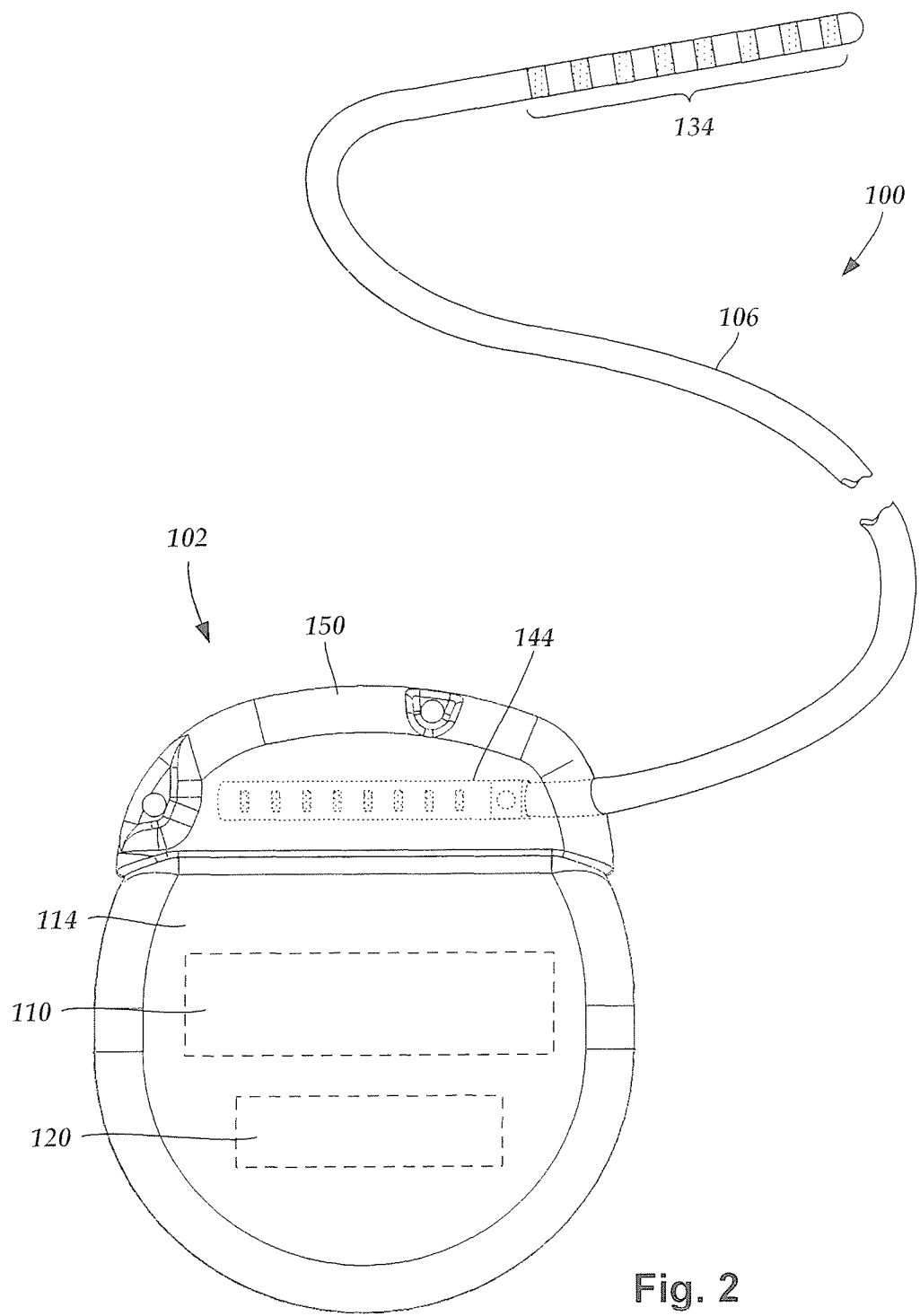
FIG. 2 is a schematic view of another embodiment of an electrical stimulation system that includes a percutaneous lead coupled to the control module of FIG. 1, according to the invention.

It will be understood that the electrical stimulation system can include more, fewer, or different components and can have a variety of different configurations including those configurations disclosed in the electrical stimulation system references cited herein. For example, instead of a paddle body 104, the electrodes 134 can be disposed in an array at or near the distal end of the lead body 106 forming a percutaneous lead, as illustrated in FIG. 2. A percutaneous lead may be isodiametric along the length of the lead body 106.

The electrical stimulation system or components of the electrical stimulation system, including one or more of the lead bodies 106, the control module 102, and, in the case of a paddle lead, the paddle body 104, are typically implanted into the body of a patient. The electrical stimulation system can be used for a variety of applications including, but not limited to, spinal cord stimulation, brain stimulation, neural stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, titanium, or rhenium.

The number of electrodes 134 in the array of electrodes 134 may vary. For example, there can be two, three, four, five, six, seven, eight, nine, ten, eleven, twelve, thirteen, fourteen, fifteen, sixteen, or more electrodes 134. As will be recognized, other numbers of electrodes 134 may also be used. As will be recognized, other numbers of electrodes 134 may also be used. In FIG. 1, sixteen electrodes 134 are shown. The electrodes 134 can be formed in any suitable shape including, for example, round, oval, triangular, rectangular, pentagonal, hexagonal, heptagonal, octagonal, or the like.

The electrodes of the paddle body 104 or one or more lead bodies 106 are typically disposed in, or separated by, a non-conductive, biocompatible material including, for example, silicone, polyurethane, and the like or combinations thereof. The paddle body 104 and one or more lead bodies 106 may be formed in the desired shape by any process including, for example, molding (including injection molding), casting, and the like. Electrodes and connecting wires can be disposed onto or within a paddle body either prior to or subsequent to a molding or casting process. The non-conductive material typically extends from the distal end of the lead to the proximal end of each of the one or more lead bodies 106. The non-conductive, biocompatible material of the paddle body 104 and the one or more lead bodies 106 may be the same or different. The paddle body 104 and the one or more lead bodies 106 may be a unitary structure or can be formed as two separate structures that are permanently or detachably coupled together.

Terminals (e.g., 310 in FIGS. 3A-3C) are typically disposed at the proximal end of the one or more lead bodies 106 for connection to corresponding conductive contacts (e.g., 316 in FIGS. 3A-3B; and 340 of FIG. 3C) in connector assemblies (e.g., 144 in FIGS. 1-3C) disposed on, for example, the control module 102 (or to other devices, such as conductive contacts on a lead extension, an operating room cable, a splitter, an adaptor, or the like).

Conductive wires (not shown) extend from the terminals (e.g., 310 in FIGS. 3A-3C) to the electrodes 134. Typically, one or more electrodes 134 are electrically coupled to a terminal (e.g., 310 in FIGS. 3A-3C). In some embodiments, each terminal (e.g., 310 in FIGS. 3A-3C) is only coupled to one electrode 134.

The conductive wires may be embedded in the non-conductive material of the lead or can be disposed in one or more lumens (not shown) extending along the lead. In some embodiments, there is an individual lumen for each conductive wire. In other embodiments, two or more conductive wires may extend through a lumen. There may also be one or more lumens (not shown) that open at, or near, the proximal end of the lead, for example, for inserting a stylet rod to facilitate placement of the lead within a body of a patient. Additionally, there may also be one or more lumens (not shown) that open at, or near, the distal end of the lead, for example, for infusion of drugs or medication into the site of implantation of the paddle body 104. In at least one embodiment, the one or more lumens may be flushed continually, or on a regular basis, with saline, epidural fluid, or the like. In at least some embodiments, the one or more lumens can be permanently or removably sealable at the distal end.

As discussed above, the one or more lead bodies 106 may be coupled to the one or more connector assemblies 144 disposed on the control module 102. The control module 102 can include any suitable number of connector assemblies 144 including, for example, two three, four, five, six, seven, eight, or more connector assemblies 144. It will be understood that other numbers of connector assemblies 144 may be used instead. In FIG. 1, each of the two lead bodies 106 includes eight terminals that are shown coupled with eight conductive contacts disposed in a different one of two different connector assemblies 144.

Figure 3A:
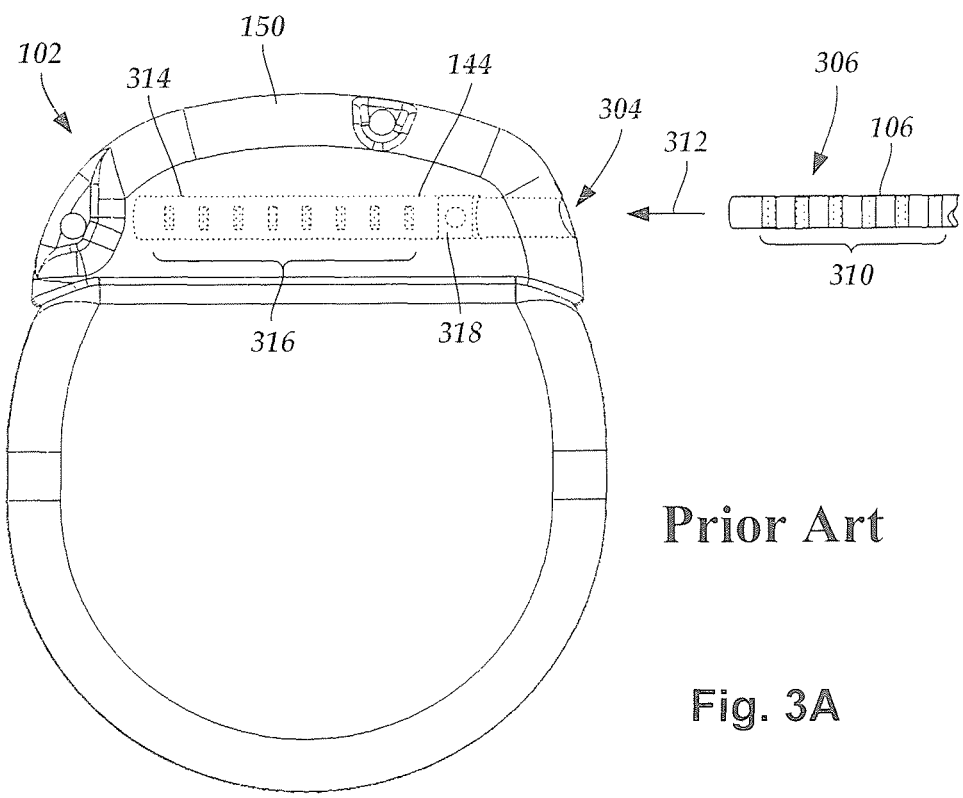
FIG. 3A is a schematic view of one embodiment of a connector assembly disposed in the control module of FIG. 1, the connector assembly configured and arranged to receive the proximal portion of one of the lead bodies of FIG. 1, according to the invention.
Figure 3B:
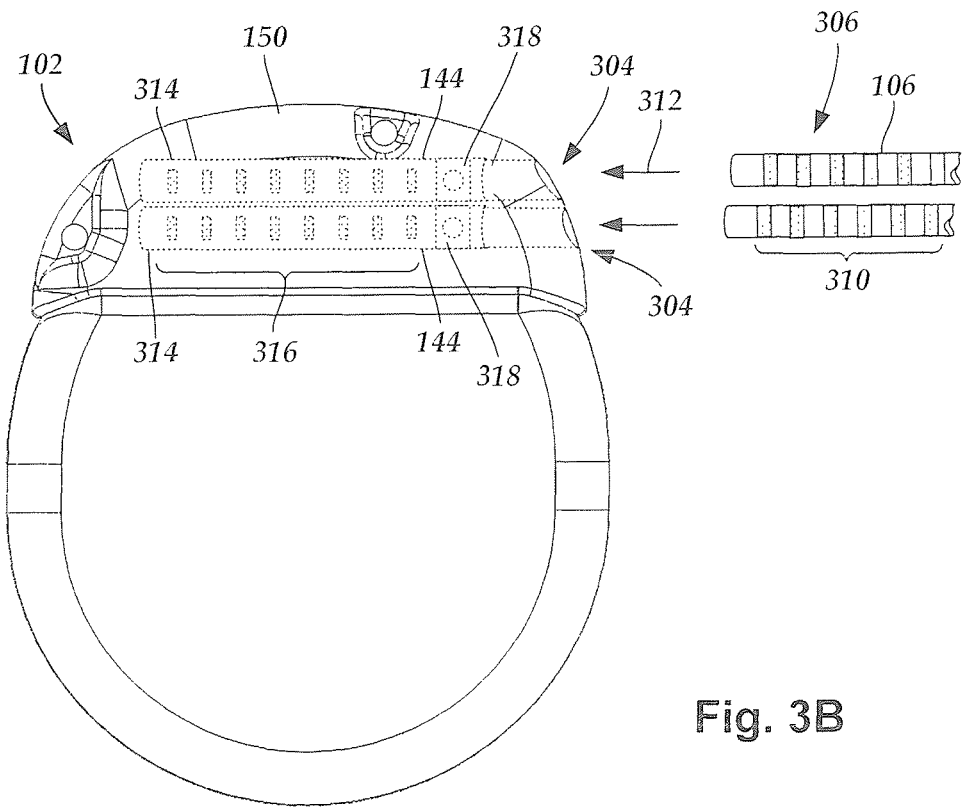
FIG. 3B is a schematic view of one embodiment of a plurality of connector assemblies disposed in the control module of FIG. 1, the connector assemblies configured and arranged to receive the proximal portions of the lead bodies of FIG. 1, according to the invention.

In at least some embodiments, leads are coupled to connectors disposed on control modules. FIG. 3A is a schematic perspective view of one embodiment of a single connector assembly 144 disposed on the control module 102. FIG. 3B is a schematic perspective view of one embodiment of a plurality of connector assemblies 144 disposed on the control module 102. In at least some embodiments, the control module 102 includes two connector assemblies 144. In at least some embodiments, the control module 102 includes four connector assemblies 144.

In FIGS. 3A and 3B, the proximal ends 306 of one or more lead bodies 106 are shown configured and arranged for insertion to the control module 102. In FIGS. 3A and 3B, the one or more connector assemblies 144 are disposed in the header 150. In at least some embodiments, the header 150 defines one or more ports 304 into which a proximal end 306 of the one or more lead bodies 106 with terminals 310 can be inserted, as shown by directional arrows 312, in order to gain access to the connector contacts disposed in the one or more connector assemblies 144.

The one or more connector assemblies 144 each include a connector housing 314 and a plurality of connector contacts 316 disposed therein. Typically, the connector housing 314 defines a port (not shown) that provides access to the plurality of connector contacts 316. In at least some embodiments, one or more of the connector assemblies 144 further includes a retaining element 318 configured and arranged to fasten the corresponding lead body 308 to the connector assembly 144 when the lead body 106 is inserted into the connector assembly 144 to prevent undesired detachment of the lead body 106 from the connector assembly 144. For example, the retaining element 318 may include an aperture through which a fastener (e.g., a set screw, pin, or the like) may be inserted and secured against an inserted lead body or lead extension.

When the one or more lead bodies 106 are inserted into the one or more ports 304, the connector contacts 316 can be aligned with the terminals 310 disposed on the one or more lead bodies 106 to electrically couple the control module 102 to the electrodes (134 of FIG. 1) disposed at a distal end of the one or more lead bodies 106. Examples of connector assemblies in control modules are found in, for example, U.S. Pat. Nos. 7,244,150 and 8,224,450, which are incorporated by reference.

Figure 3C:
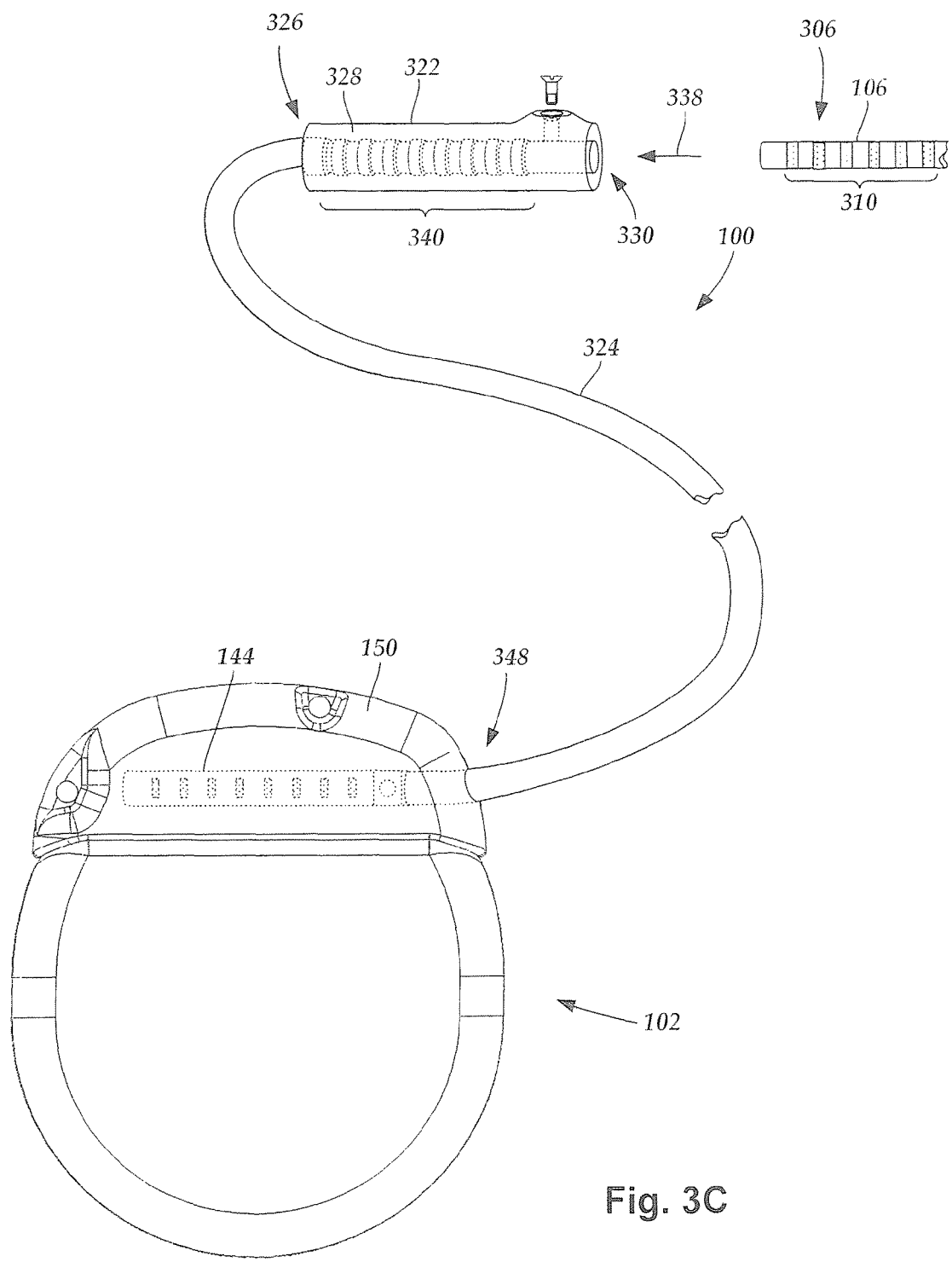
FIG. 3C is a schematic view of one embodiment of a proximal portion of one of the lead bodies of FIG. 1, a lead extension, and the control module of FIG. 1, the lead extension configured and arranged to couple the lead body to the control module, according to the invention.

In FIG. 3C, a lead extension connector assembly 322 is disposed on a lead extension 324. The lead extension connector assembly 322 is shown disposed at a distal end 326 of the lead extension 324. The lead extension connector assembly 322 includes a contact housing 328. The contact housing 328 defines at least one port 330 into which a proximal end 306 of the lead body 106 with terminals 310 can be inserted, as shown by directional arrow 338. The lead extension connector assembly 322 also includes a plurality of connector contacts 340. When the lead body 106 is inserted into the port 330, the connector contacts 340 disposed in the contact housing 328 can be aligned with the terminals 310 on the lead body 106 to electrically couple the lead extension 324 to the electrodes (134 of FIG. 1) disposed at a distal end (not shown) of the lead body 106.

The proximal end of a lead extension can be similarly configured and arranged as a proximal end of a lead body. The lead extension 324 may include a plurality of conductive wires (not shown) that electrically couple the connector contacts 340 to a proximal end 348 of the lead extension 324 that is opposite to the distal end 326. The conductive wires disposed in the lead extension 324 can be electrically coupled to a plurality of terminals (not shown) disposed on the proximal end 348 of the lead extension 324. In at least some embodiments, the proximal end 348 of the lead extension 324 is configured and arranged for insertion into a lead extension connector assembly disposed in another lead extension. In other embodiments (as shown in FIG. 3C), the proximal end 348 of the lead extension 324 is configured and arranged for insertion into the connector assembly 144 disposed on the control module 102.

Conventional electrical stimulation systems may be potentially unsafe for use with magnetic resonance imaging ("MRI") due to the effects of electromagnetic fields in an MRI environment. A common mechanism for causing the electrical interactions between the electrical stimulation system and RF irradiation is common-mode coupling of the applied electromagnetic fields that act as a series of distributed sources along elongated conductive structures, such as leads, or conductors within leads. Common-mode induced RF currents can reach amplitudes of greater than one ampere in MRI environments. Such currents can cause heating and potentially disruptive voltages within electronic circuits.

Some of the effects of RF irradiation may include, for example, inducing current in the lead, causing undesired heating of the lead that may potentially cause tissue damage, undesired or unexpected operation of electronic components, or premature failure of electronic components. Additionally, when an electrical stimulation system is used within an MRI scanner environment, the electrical interactions between the electrical stimulation system and the MRI may cause distortions in images formed by the MRI system.

Figure 4A:
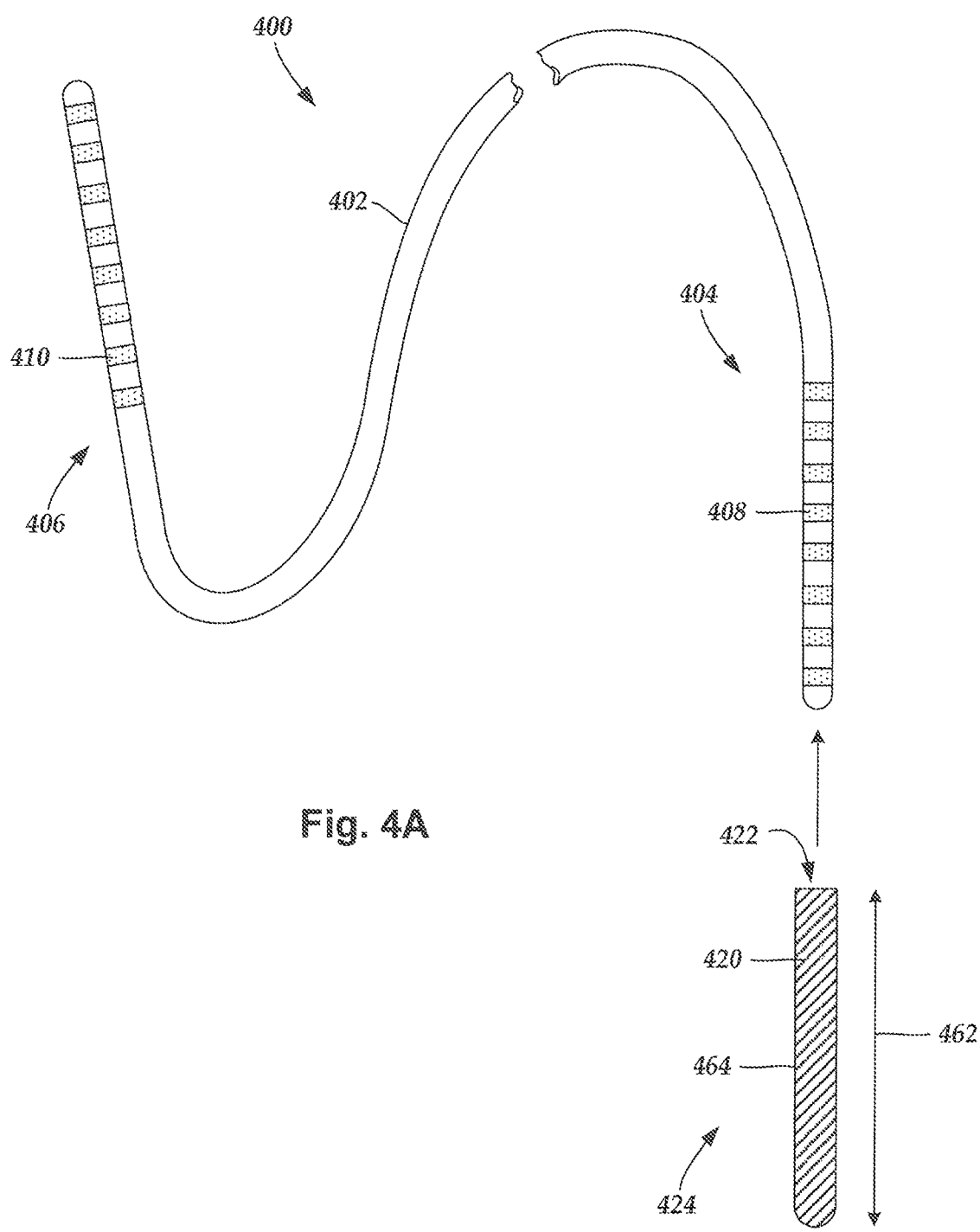
FIG. 4A is a schematic side view of one embodiment of a lead and a safety device configured and arranged for insertion over a portion of the lead, according to the invention.

Turning to FIG. 4A, as herein described a current-limiting arrangement may be used for reducing risk associated with exposure of a patient with an implanted lead to RF energy, such as RF energy experienced during an MRI procedure. In at least some embodiments, the current-limiting arrangement includes a safety device that reduces or prevents tissue overheating at positions near one or more portions of the lead, such as near the distal portion of the lead in proximity to the electrodes. In at least some embodiments, the safety device reduces or prevents undesired tissue stimulation by the lead caused by environmental exposure to RF energy.

In some instances, a single safety device may be used. In other instances, a plurality of safety devices may be used. In some embodiments, the one or more safety devices are configured and arranged to couple with a single lead body. In other embodiments, the one or more safety devices are configured and arranged to couple with a plurality of lead bodies from either a single implanted lead or a plurality of implanted leads.

In some instances, the lead may be implanted in the patient such that the proximal end of the lead is coupled to the control module (see e.g., FIGS. 1 and 2). In which case, the control module may be uncoupled from the lead prior to coupling the safety device to the lead. When the control module is implanted in the patient, physical access to the control module may be needed to uncouple the lead from the control module. When, for example, the control module is disposed in a subdermal pocket of patient tissue, a medical practitioner may perform a small incision in the patient to gain physical access to the control module to uncouple the lead from the control module.

In other instances, the lead may be implanted in the patient such that the lead is not coupled to the control module. For example, the lead may be an abandoned lead, where the lead is no longer operating (and is uncoupled from the control module) but has been left in place to avoid risks to the patient associated with removal of the lead. In which case, the control module may or may not be present in the patient. As another example, the lead may be recently (or currently in the process of being) inserted into the patient. In which case, the control module may not yet be coupled to the lead.

In at least some embodiments, the safety device is coupled to the lead for the remaining implanted lifetime of the lead. For example, in the case of abandoned leads it may be desirable for the safety device to remain coupled to the lead for the remaining implanted lifetime of the lead. In which case, in at least some embodiments the safety device may be disposed in the subcutaneous pocket within which the control module was formerly disposed.

In other embodiments, the safety device is coupled to the lead for a period of time that is significantly less than the remaining implanted lifetime of the lead (i.e., the safety device is implanted for a temporary period of time). For example, the safety device may be coupled to the lead for a period of time that is no greater than three months, two months, one month, three weeks, two weeks, one week, five days, three days, or one day. In at least some embodiments, the safety device may be coupled to the lead for no more than the duration of an MRI procedure.

Figure 6A:
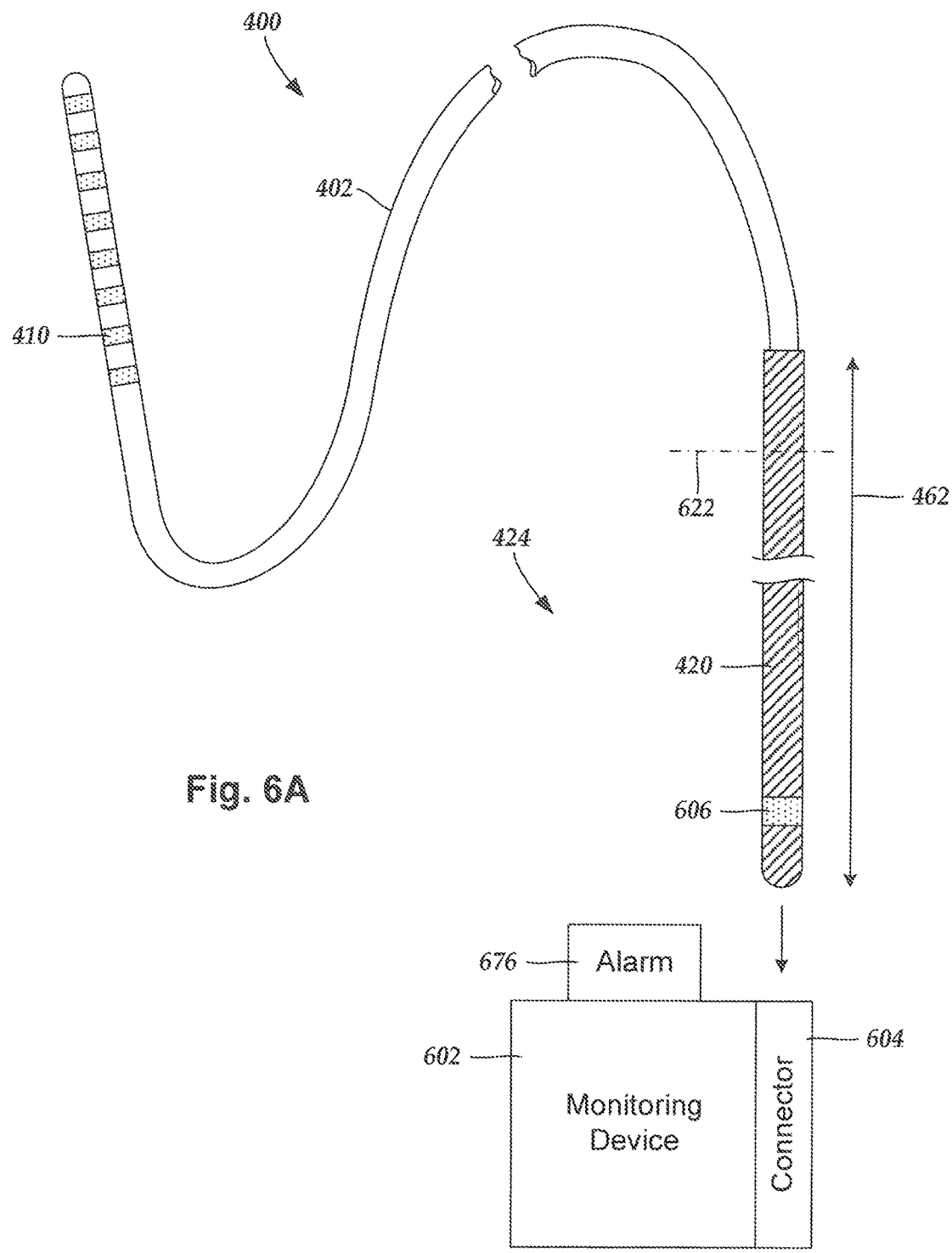
FIG. 6A is a schematic side view of another embodiment of the safety device of FIG. 4A disposed over a portion of the lead of FIG. 4A, the safety device configured and arranged for extending externally from the patient and coupling with an external monitoring device, according to the invention.
Figure 6B:
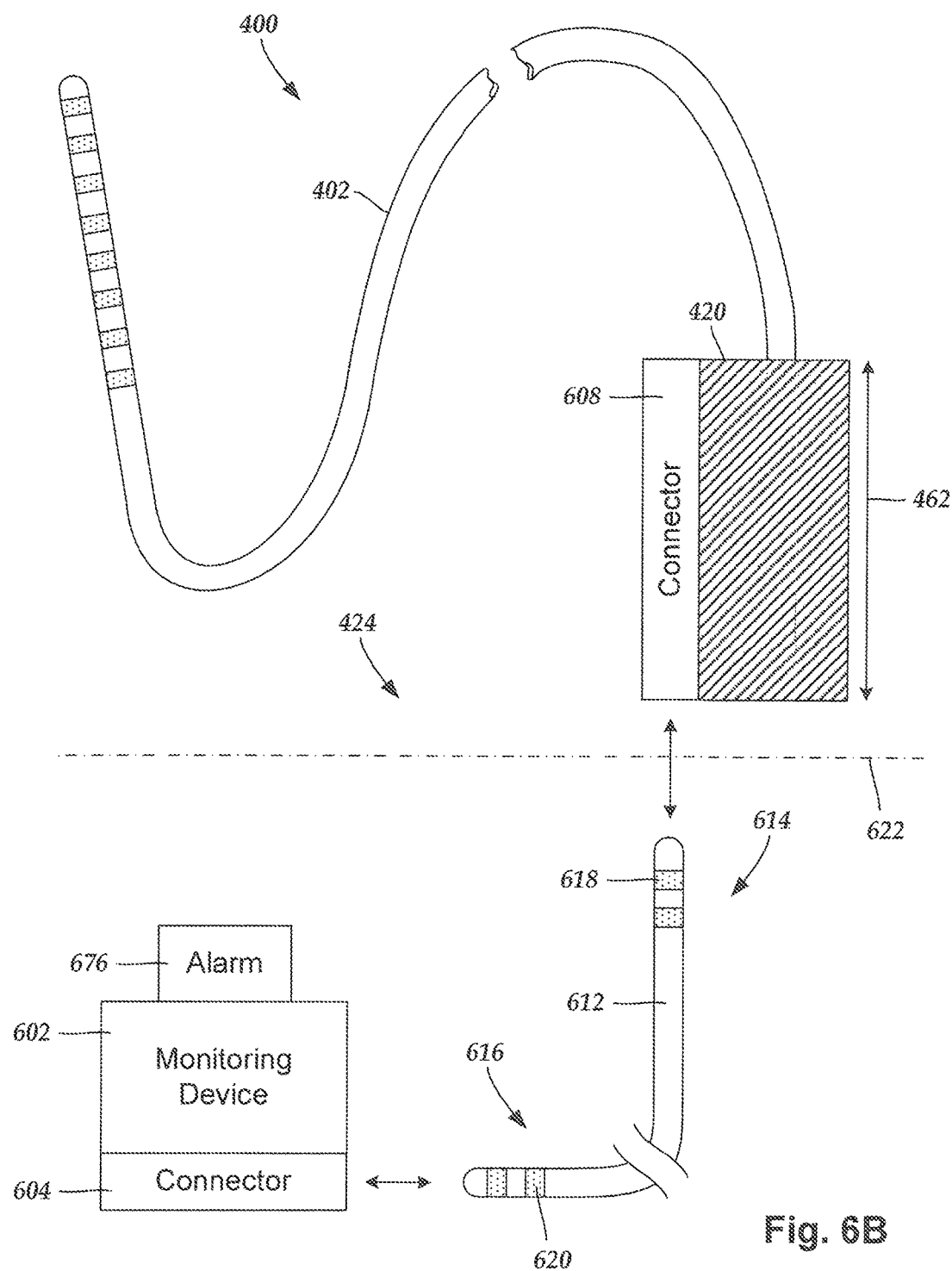
FIG. 6B is a schematic side view of another embodiment of the safety device of FIG. 4A disposed over a portion of the lead of FIG. 4A, the safety device configured and arranged for coupling with the monitoring device of FIG. 6A via a cable, according to the invention.

In at least some embodiments, the safety device is completely disposed in the patient during use (see e.g., FIG. 6B). It may be advantageous for the safety device to remain completely disposed in the patient during use to maintain sterility of the safety device during use. It may be particularly advantageous for the safety device to be completely disposed in the patient during use in embodiments where the safety device is to remain coupled to the lead for the remaining implantable lifetime of the lead. In at least some embodiments, the safety device forms a termination for the lead.

In embodiments where the safety device is implanted for a temporary period of time, and where an incision was made to access the lead, the incision may be temporarily closed for at least the duration of the imaging procedure. In some cases, the patient may undergo multiple MRI procedures spread out over a period or several hours, days, weeks, or months. In which case, when the temporary period of time exceeds the time length of the imaging procedure, the patient may, in at least some embodiments return to a medical practitioner at a later date for removal of the safety device and reattachment of the control module.

In at least some other embodiments, the safety device is disposed completely external to the patient during use. For example, in at least some embodiments the safety device may used during a trial stimulation prior to complete implantation of the electrical stimulation system. In which case, the portion of the lead to which the safety device is coupled may, optionally, be at least partially externalized from the patient. In at least some embodiments, the safety device is partially disposed in the patient during use and partially disposed external to the patient (see e.g., FIG. 6A).

In at least some embodiments, the current-limiting arrangement includes one or more monitoring devices coupled to the safety device (see e.g., FIGS. 6A-6B). The monitoring device may be disposed external to the patient. In at least some embodiments, the safety device couples directly with the monitoring device (see e.g., FIG. 6A). In other embodiments, the current-limiting arrangement includes one or more cables that physically couple the safety device to the monitoring device (see e.g., FIG. 6B).

FIG. 4A is a schematic side view of one embodiment of a lead 400 having a lead body 402 with a proximal end 404 and a distal end 406. A plurality of terminals, such as terminal 408, are disposed at the proximal end 404 and a plurality of electrodes, such as electrode 410, are disposed at the distal end 406. A safety device 420 of a current-limiting arrangement 424 is configured and arranged for coupling with the lead body 402. The safety device 420 is also configured and arranged for reducing risk associated with exposure of a patient within which the implanted lead 400 is disposed to RF energy, such as RF energy experienced during an MRI procedure.

The safety device 420 has a length 462 and an outer surface 464. The safety device 420 defines at least one port 422 that extends along the length 462 of the safety device 420 and that is configured and arranged for receiving a portion of the lead body 402. In at least some embodiments, the safety device 420 is configured and arranged for insertion over at least a portion of the proximal end 404 of the lead 402.

Figure 4B:
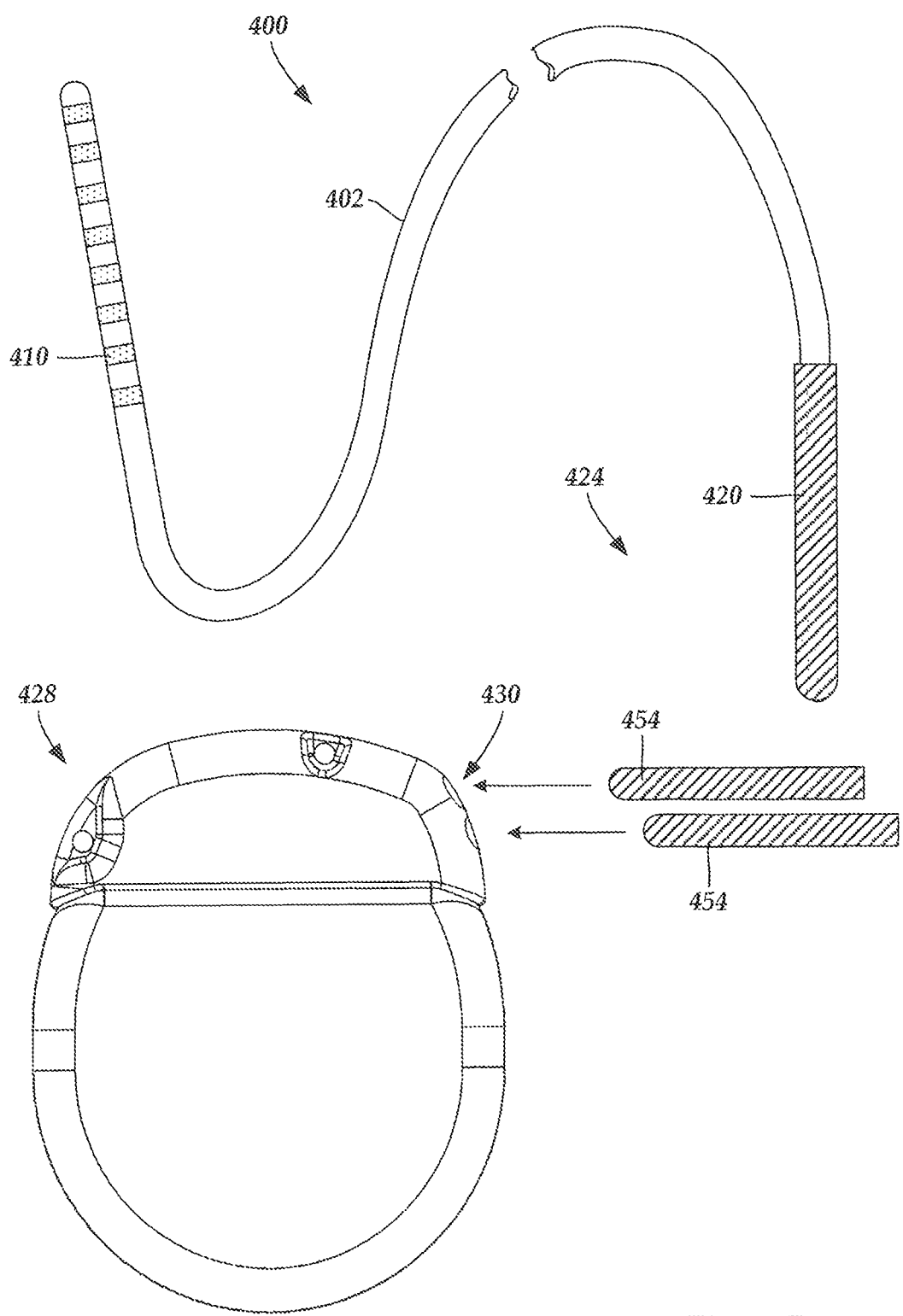
FIG. 4B is a schematic side view of one embodiment of the safety device of FIG. 4A disposed over a portion of the lead of FIG. 4A and plugs insertable into ports of a control module, according to the invention.

FIG. 4B is a schematic side view of one embodiment of the safety device 420 disposed over the proximal end of the lead body 402. In at least some embodiments, the safety device 420 is disposed over the proximal end of the lead body 402 with the safety device 420 completely covering each of the terminals 408, such that the terminals are not directly exposed to patient tissue.

In at least some embodiments where a control module 428 is disposed in the patient during an MRI procedure, the control module 428, as well as patient tissue surrounding the control module 428, may also be adversely affected by exposure to applied electromagnetic fields. In at least some embodiments, the current-limiting arrangement 424 includes one or more plugs, or covers, or both configured and arranged for insertion into one or more ports 430 of the control module 428. In FIG. 4B, plugs 454 are shown configured and arranged for insertion into the ports 430. In at least some embodiments, the safety device 420 is configured and arranged for mounting to the control module 428 while the safety device is inserted in the patient.

In at least some embodiments, the one or more plugs are disposed at the proximal end of the safety device 420. In at least some embodiments, the safety device 420 is in-line with the lead body 402 and the control module 428 such that one end of the safety device 420 receives the proximal end of the lead body 402 while an opposing end of the safety device 420 plugs into the control module 428.

Figure 5:
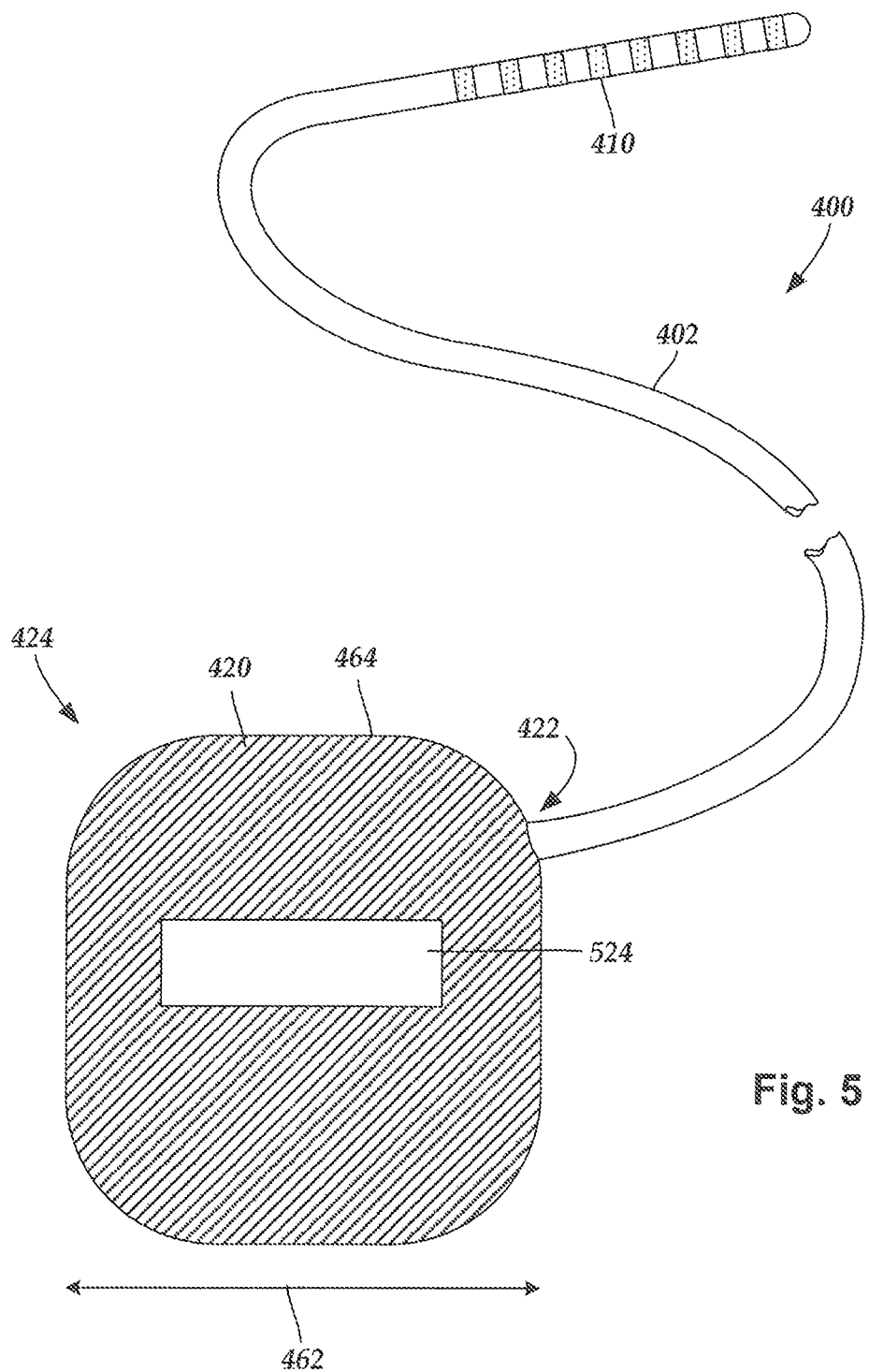
FIG. 5 is a schematic side view of another embodiment of the safety device of FIG. 4A with a different shape, the safety device including an electronic subassembly, according to the invention.

In FIGS. 4A and 4B, the safety device 420 is shown as being tubular-shaped. It will be understood that the safety device 420 can be formed in any suitable shape including, for example, round, oval, disc-shaped, triangular, rectangular, pentagular, or the like. FIG. 5 is a schematic side view of one embodiment of the safety device 420 formed in a flat, rectangular shape. In FIG. 5, the lead body 402 is shown inserted into the port 422 of the safety device 420. In at least some embodiments, the safety device 420 defines a plurality of ports for receiving portions of a plurality of lead bodies from one or more leads. The safety device 420 can include any suitable number of ports including, for example, one, two, three, four, five, six, seven, eight, or more ports.

The safety device 420 can be formed in any suitable size. In FIGS. 4A and 4B the safety device 420 is shown as having a diameter that is large enough to receive the proximal end 404 of the lead body 402. In at least some embodiments, the insertion length 462 of the safety device 420 is long enough to cover all of the terminals 408 when the proximal end 404 of the lead body 402 is inserted into the safety device 420. In FIG. 5, the safety device 420 is shown as having dimensions that are similar to the control module (428 in FIG. 4B). It may be an advantage to form the safety device 420 with dimensions similar to the control module so that, in embodiments where the safety device is inserted into the patient, the safety device can be disposed next to the control module, or in the space where the control module formerly was disposed prior to removal. In at least some embodiments, the safety device is formed such that the largest dimension (e.g., the insertion length 462) of the safety device is not greater than 10 cm, 9 cm, 8 cm, 7 cm, 6 cm, or 5 cm.

In at least some embodiments, the safety device provides an impedance value sufficient to dissipate RF energy propagating along the lead (or coupled lead extension, or both) to a level that prevents overheating of tissue near one or more portions of the lead, such as the distal portion of the lead in proximity to the electrodes 410. In at least some embodiments, the safety device provides an impedance value sufficient to dissipate RF energy propagating along the lead to a level that prevents undesired tissue stimulation.

In at least some embodiments, the safety device presents a general impedance of at least 50, 60, 70, 80 ohms, or more at one RF frequency, multiple RF frequencies, or over a range of RF frequencies utilized by MRI systems during MRI procedures. MRI systems may use different ranges of RF frequencies (i.e., MRI RF frequencies) including, for example, 64 MHz, 85 MHz, or 128 MHz. In at least some embodiments, the safety device additionally includes one or more low-impedance pathways (e.g., a pathway that presents an impedance of no greater than 50, 40, 30 ohms, or less at one RF frequency, multiple RF frequencies, or over a range of RF frequencies utilized by MRI systems during MRI procedures).

In at least some embodiments, the safety device includes an electronic subassembly 524 that includes circuitry, or one or more filters, or both, for removing or redirecting current propagating along the lead, when the safety device 420 is coupled to the lead 402. Such circuitry (or filters, or both) may include one or more resistors, capacitors, inductors, or the like. In at least some embodiments, the filters may be tuned to a specific range of RF frequencies that include the range of RF frequencies used during an MRI procedure.

The safety device 420 can be formed from any material suitable for implantation in a patient including, for example, silicone, epoxies, urethanes, PEEK, ceramics, plastics, rubbers, metals, alloys, or the like or combinations thereof. In at least some embodiments, the safety device is formed such that it will not generate a significant amount of heating during an MRI procedure (where the safety device may be exposed to significant forces and torques). One way of achieving this is by forming the safety device primarily from relatively non-conducting materials including, for example, silicone, epoxies, urethanes, PEEK, ceramics, plastics, rubbers, or the like.

In at least some embodiments, the safety device 420 is configured and arranged to form one or more closed current loops during exposure to RF energy. These closed current loops are encapsulated in thermal isolating materials to reduce or prevent heating on the outer surface 464 of the safety device. The outer surface 464 can be formed from conductive material (e.g., electrically conductive), non-conductive material (e.g., electrically non-conductive), or a combination of both conductive material and non-conductive material. In at least some embodiments, the selection of conductive, non-conductive, or conductive and non-conductive materials can be arranged along the outer surface 464 of the safety device to reduce or prevent the formation of closed current loops large enough to harm the patient during typical MRI procedure conditions. In at least some embodiments, when conductive materials are arranged along the outer surface 464 of the safety device, one or more thermal isolating materials (e.g., silicone, epoxy, urethane, PEEK, one or ceramics, plastics, rubbers, or the like) may be disposed over the conductive material to reduce, or even prevent, heating along the outer surface 464. In at least some embodiments, forming at least a portion of the outer surface 464 of the safety device from one or more conductive materials may be used to provide a return path for current when, for example, one or more filters are incorporated into the safety device.

Turning to FIGS. 6A-6B, in at least some embodiments the safety device is configured to couple with one or more devices disposed external to the patient, such as one or more monitoring devices. In at least some embodiments, the safety device couples remotely to the external device. In at least some other embodiments, the safety device couples directly with the external device. In at least some other embodiments, one or more cables (e.g., lead extensions, operating room cables, or the like) couple the safety device to the monitoring device. In some instances, a sterile end of the one or more cables may be attached to the safety device while the remaining portions of the one or more cables are externalized in a non-sterile environment for temporary use.

FIG. 6A is a schematic side view of another embodiment of the lead 400 and the current-limiting arrangement 424. The current-limiting arrangement 424 includes the safety device 420 disposed over a portion of the lead body 402. In FIG. 6A, the safety device 420 is shown configured and arranged for extending externally from the patient and coupling with one or more monitoring devices 602 disposed external to the patient. In at least some embodiments, the safety device 420 is configured and arranged for coupling directly with one or more other monitoring devices 602. The monitoring device 602 may, optionally, include a connector 604 for receiving a portion of the safety device 420. The portion of the safety device 420 that is received by the monitoring device may include one or more contacts 606 for providing an electrical connection with the monitoring device 602 when the safety device 420 is received by the connector 604. In at least some embodiments, the monitoring device 602 includes a ground for current redirected away from the lead 400 by the safety device 420.

FIG. 6B is a schematic side view of yet another embodiment of the lead 400 and the current-limiting arrangement 424. The current-limiting arrangement 424 includes the safety device 420 disposed over a portion of the lead body 402. The safety device 420 includes a connector 608. A cable 612 having a proximal end 614 and a distal end 616 is configured and arranged to couple the safety device 420 to the monitoring device 602. In FIG. 6B, one or more proximal contacts 618 are shown disposed on the proximal end 614 of the cable 612 and one or more distal contacts 620 are shown disposed on the distal end 616 of the cable 612. In at least some embodiments, the connector 608 of the safety device 420 is configured to receive the one or more proximal contacts 618 and the connector 604 of the monitoring device 602 is configured to receive the one or more distal contacts 620.

In FIGS. 6A-6B, a line 622 marks an interface between the patient and the environment external to the patient. In FIG. 6A, the interface 622 is disposed somewhere along the length 462 of the safety device 420. In FIG. 6A, the interface is disposed beyond the safety device 420, indicating that the entire safety device 420 is disposed within the patient when the cable 612 is coupled to the safety device 420. In at least some alternate embodiments, at least a portion of the safety device 420 may be disposed external to the patient when the cable 612 is coupled to the safety device 420.

The monitoring device 602 can be any suitable device for monitoring the safety device, the patient, or both. In at least some embodiments, the monitoring device 602 includes one or more displays for displaying monitored data. In other embodiments, the monitoring device 602 is configured and arranged to transmit received data to one or more other devices, such as one or more work stations. Such transmissions may propagate via any suitable mode, such as one or more wires, wireless (e.g., RF telemetry), or optical communication (e.g., with fiber optics).

In at least some embodiments the monitoring device 602 monitors the safety device. In which case, the monitoring device 602 may, for example, monitor one or more of: attachment of the safety device to the lead; one or more conditions of the safety device itself (e.g., checking for broken wires, short-circuits, or the like); one or more conditions experienced (either currently, or previously, or both) by the safety device (e.g., RF currents, gradient currents, temperature measurements, vibration, acceleration, movement, forces, or the like). In at least some embodiments, the monitoring device 602 monitors one or more patient parameters including, for example, pulse, blood pressure, heart rhythm/rate, breathing rate, temperature, or the like.

In at least some embodiments, the monitoring device 602 records at least some of the monitoring data collected for subsequent evaluation. In at least some embodiments, the monitoring device 602 includes one or more alarms (e.g., auditory, visual, tactile, olfactory, or the like) 676 which are activated upon detection of one or more potentially unsafe conditions experienced by the safety device (e.g., excessive RF currents, excessive gradient currents, excessive thermal increase, excessive vibration, excessive acceleration, excessive movement, or the like). In at least some embodiments, the one or more alarms 676 are configured and arranged to activate upon detection of one or more patient parameters outside of a predetermined range. Optionally, the one or more alarms 676 may be patient- or medical practitioner-activated.

The safety device, the monitoring device, or both may include one or more actuators for use by the patient during RF exposure to indicate whether or not the patient is able to continue with the RF exposure. In at least some embodiments, the safety device, the monitoring device, or both may include one or more actuators for use by the patient (or one or more medical practitioners) to reduce, or eliminate, RF exposure upon activation of the one or more actuators. Any suitable type of actuator(s) may be used including, for example, one or more switches, audio signals (e.g., audio amplification and transmission of patient voice commands), or the like.

In at least some embodiments, the monitoring device 602 is disconnected from the safety device 420 during an MRI procedure. In other embodiments, the monitoring device 602 remains connected with the safety device 420 during an MRI procedure. In which case, the monitoring device 602 may include, for example, an isolation circuit to remain electrically isolated from the safety device during the MRI procedure.

In FIGS. 4A-6B, a percutaneous lead with a single lead body is shown. The safety devices disclosed herein are equally suitable for use with any other electrical stimulation leads including, for example, percutaneous leads with a plurality of lead bodies, paddle leads (see e.g., FIG. 1), cuff leads, or the like.

Figure 7:
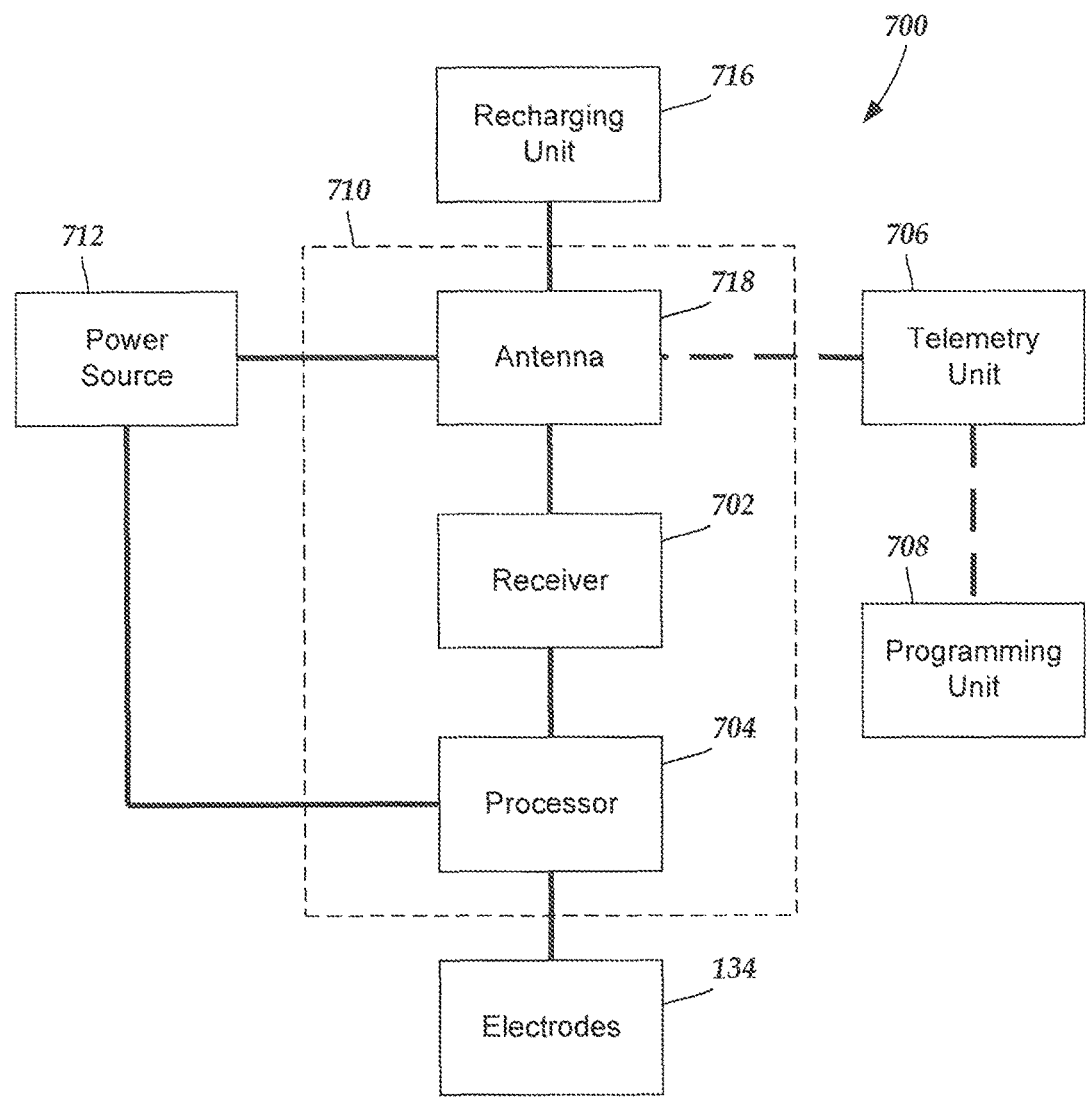
FIG. 7 is a schematic overview of one embodiment of components of a stimulation system, including an electronic subassembly disposed within a control module, according to the invention.

FIG. 7 is a schematic overview of one embodiment of components of an electrical stimulation system 700 including an electronic subassembly 710 disposed within a control module. It will be understood that the electrical stimulation system can include more, fewer, or different components and can have a variety of different configurations including those configurations disclosed in the stimulator references cited herein.

Some of the components (for example, power source 712, antenna 718, receiver 702, and processor 704) of the electrical stimulation system can be positioned on one or more circuit boards or similar carriers within a sealed housing of an implantable pulse generator, if desired. Any power source 712 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference.

As another alternative, power can be supplied by an external power source through inductive coupling via the optional antenna 718 or a secondary antenna. The external power source can be in a device that is mounted on the skin of the user or in a unit that is provided near the user on a permanent or periodic basis.

If the power source 712 is a rechargeable battery, the battery may be recharged using the optional antenna 718, if desired. Power can be provided to the battery for recharging by inductively coupling the battery through the antenna to a recharging unit 716 external to the user. Examples of such arrangements can be found in the references identified above.

In one embodiment, electrical current is emitted by the electrodes 134 on the paddle or lead body to stimulate nerve fibers, muscle fibers, or other body tissues near the electrical stimulation system. A processor 704 is generally included to control the timing and electrical characteristics of the electrical stimulation system. For example, the processor 704 can, if desired, control one or more of the timing, frequency, strength, duration, and waveform of the pulses. In addition, the processor 704 can select which electrodes can be used to provide stimulation, if desired. In some embodiments, the processor 704 may select which electrode(s) are cathodes and which electrode(s) are anodes. In some embodiments, the processor 704 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 708 that, for example, allows modification of pulse characteristics. In the illustrated embodiment, the processor 704 is coupled to a receiver 702 which, in turn, is coupled to the optional antenna 718. This allows the processor 704 to receive instructions from an external source to, for example, direct the pulse characteristics and the selection of electrodes, if desired.

In one embodiment, the antenna 718 is capable of receiving signals (e.g., RF signals) from an external telemetry unit 706 which is programmed by a programming unit 708. The programming unit 708 can be external to, or part of, the telemetry unit 706. The telemetry unit 706 can be a device that is worn on the skin of the user or can be carried by the user and can have a form similar to a pager, cellular phone, or remote control, if desired. As another alternative, the telemetry unit 706 may not be worn or carried by the user but may only be available at a home station or at a clinician's office. The programming unit 708 can be any unit that can provide information to the telemetry unit 706 for transmission to the electrical stimulation system 700. The programming unit 708 can be part of the telemetry unit 706 or can provide signals or information to the telemetry unit 706 via a wireless or wired connection. One example of a suitable programming unit is a computer operated by the user or clinician to send signals to the telemetry unit 706.

The signals sent to the processor 704 via the antenna 718 and receiver 702 can be used to modify or otherwise direct the operation of the electrical stimulation system. For example, the signals may be used to modify the pulses of the electrical stimulation system such as modifying one or more of pulse duration, pulse frequency, pulse waveform, and pulse strength. The signals may also direct the electrical stimulation system 700 to cease operation, to start operation, to start charging the battery, or to stop charging the battery. In other embodiments, the stimulation system does not include an antenna 718 or receiver 702 and the processor 704 operates as programmed.

Optionally, the electrical stimulation system 700 may include a transmitter (not shown) coupled to the processor 704 and the antenna 718 for transmitting signals back to the telemetry unit 706 or another unit capable of receiving the signals. For example, the electrical stimulation system 700 may transmit signals indicating whether the electrical stimulation system 700 is operating properly or not or indicating when the battery needs to be charged or the level of charge remaining in the battery. The processor 704 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. An implantable lead assembly for an electrical stimulation system, the lead assembly comprising:
 a first lead configured and arranged for insertion into a patient, the first lead comprising
  a lead body having a distal end portion, a proximal end portion, and a longitudinal length,
  a plurality of electrodes disposed along the distal end portion of the lead body,
  a plurality of terminals disposed along the proximal end portion of the lead body, and a plurality of conductors electrically coupling the plurality of electrodes to the plurality of terminals; and
a current-limiting arrangement coupleable with the first lead, the current-limiting arrangement configured and arranged for limiting the amount of RF-induced current propagating along the lead body during an MRI procedure, the current-liming arrangement comprising
a safety device configured and arranged to couple to the lead body when the lead body is implanted in the patient, the safety device having a length and an outer surface, the safety device defining a first port extending along the length of the safety device, the first port configured and arranged for receiving the proximal end portion of the lead body and for covering each of the plurality of terminals to prevent the plurality of terminals from contacting patient tissue, wherein the safety device provides an impedance of at least 50 ohms at one or more MRI RF frequencies, and
a monitoring device coupleable to the safety device and comprising an alarm configured and arranged for activating when the monitoring device detects a potentially unsafe condition being experienced by the safety device.

2. The lead assembly of claim 1, wherein the safety device is configured and arranged for disposing entirely within the patient when the safety device is coupled to the lead body.

3. The lead assembly of claim 1, wherein the safety device comprises at least one filter.

4. The lead assembly of claim 1, further comprising a second lead.

5. The lead assembly of claim 1, wherein at least a portion of the outer surface of the safety device comprises a conductive material.

6. The lead assembly of claim 1, wherein at least a portion of the outer surface of the safety device comprises a non-conductive material.

7. An electrical stimulating system comprising:
the lead assembly of claim 1;
a control module configured and arranged to electrically couple to the lead body of the lead assembly, the control module comprising
a housing, and
an electronic subassembly disposed in the housing; and
at least one connector configured and arranged for receiving the lead body, the at least one connector having a first end and an opposing second end, the at least one connector comprising
a connector housing defining a port at the first end of the connector, the port configured and arranged for receiving the proximal end portion of the lead body, and
a plurality of connector contacts disposed in the connector housing, the plurality of connector contacts configured and arranged to couple to the plurality of terminals of the lead body when the lead body is inserted into the port of the connector housing.

8. The electrical stimulation system of claim 7, wherein the control module comprises the connector, the electrical stimulation system further comprising a plug configured and arranged for insertion into the port of the connector.

9. The implantable lead assembly of claim 1, wherein the safety device is configured and arranged to at least partially extend externally from the patient when the safety device is coupled to the lead body.

10. The lead assembly of claim 1, wherein the current-limiting arrangement further comprises at least one cable configured and arranged for coupling the safety device to the monitoring device.

11. The lead assembly of claim 1, wherein the monitoring device is configured and arranged to monitor attachment of the safety device to the first lead.

12. The lead assembly of claim 1, wherein the monitoring device is configured and arranged to monitor at least one condition experienced by the safety device, the at least one condition comprising at least one of RF current, gradient current, temperature, vibration, or acceleration.

13. The lead assembly of claim 1, wherein the monitoring device is configured and arranged to monitor at least one patient parameter, the at least one patient parameter comprising at least one of pulse, blood pressure, heart rhythm; heart rate, breathing rate, or temperature of the patient.

14. The lead assembly of claim 1, wherein the alarm is configured and arranged for activating when the monitoring device detects at least one patient parameter outside of a predetermined range.

15. The lead assembly of claim 1, wherein the unsafe condition that activates the alarm includes excessive RF current; excessive gradient current; or excessive thermal increase.

16. The lead assembly of claim 4, wherein the safety device further defines a second port configured and arranged receiving a portion of the second lead.

17. The lead assembly of claim 10, wherein the safety device comprises a connector configured and arranged to receive a portion of the at least one cable.

18. The lead assembly of claim 1, where the alarm is configured and arranged for activating when the monitoring device detects the potentially unsafe condition being experienced by the safety device, wherein the potentially unsafe condition is at least one of an RF current, a gradient current, a thermal increase, vibration, acceleration, or movement that, when detected, is determined to exceed a threshold level.

19. A method for protecting a patient with an implanted medical device from current propagation along the medical device during exposure to applied electromagnetic fields during an MRI procedure using the lead assembly of claim 1, the method comprising:
inserting the first lead into a patient;
coupling the safety device of the current-limiting arrangement to the lead body;
performing an MRI procedure on the patient while the safety device is coupled to the lead body of the first lead; and
removing the safety device from the lead body within three months of coupling the safety device to the lead body.

20. The method of claim 19, further comprising uncoupling the proximal end portion of the lead body from an implanted control module prior to coupling the safety device to the lead body.

* * * * *